(12) United States Patent
Hsieh

(10) Patent No.: US 10,898,314 B2
(45) Date of Patent: Jan. 26, 2021

(54) BREAST IMPLANT

(71) Applicant: Jui-Yang Hsieh, New Taipei (TW)

(72) Inventor: Jui-Yang Hsieh, New Taipei (TW)

( * ) Notice: Subject to any disclaimer, the term of this patent is extended or adjusted under 35 U.S.C. 154(b) by 0 days.

(21) Appl. No.: 16/578,888

(22) Filed: Sep. 23, 2019

(65) Prior Publication Data

US 2020/0222176 A1 Jul. 16, 2020

(30) Foreign Application Priority Data

Jan. 14, 2019 (TW) .............................. 108200594 U

(51) Int. Cl.
*A61F 2/12* (2006.01)
*A61L 27/20* (2006.01)
*A61L 27/22* (2006.01)
*A61L 27/18* (2006.01)

(52) U.S. Cl.
CPC ................. *A61F 2/12* (2013.01); *A61L 27/20* (2013.01); *A61L 27/222* (2013.01); *A61F 2250/0003* (2013.01); *A61L 27/18* (2013.01); *A61L 2430/04* (2013.01)

(58) Field of Classification Search
CPC ........................................................ A61F 2/12
USPC ......................................................... 623/7–8
See application file for complete search history.

(56) References Cited

U.S. PATENT DOCUMENTS

| | | | |
|---|---|---|---|
| 10,595,986 B2* | 3/2020 | Rehnke | A61F 2/12 |
| 2002/0038147 A1* | 3/2002 | Miller, III | A61F 2/12 623/8 |
| 2006/0224239 A1* | 10/2006 | Tiahrt | A61F 2/12 623/8 |
| 2009/0254179 A1* | 10/2009 | Burnett | A61L 27/18 623/8 |
| 2015/0351900 A1* | 12/2015 | Glicksman | A61B 90/02 623/8 |
| 2019/0247180 A1* | 8/2019 | Limem | A61F 2/12 |
| 2020/0268503 A1* | 8/2020 | Rehnke | A61F 2/12 |
| 2020/0268504 A1* | 8/2020 | Chitre | A61F 2/12 |
| 2020/0297479 A1* | 9/2020 | Van Epps | A61F 2/12 |

\* cited by examiner

*Primary Examiner* — Suzette J Gherbi
(74) *Attorney, Agent, or Firm* — Muncy, Geissler, Olds & Lowe, P.C.

(57) ABSTRACT

The breast implant of the present invention comprises a first pouch, a plurality of second pouches, and a plurality of third pouches. The first pouch has a first enclosing membrane and a first lumen formed by the first enclosing membrane. The interior of the first lumen includes a dome and a bottom portion corresponding to the dome. Each second pouch has a second enclosing membrane and a second lumen formed by the second enclosing membrane. The second pouches are provided in the first lumen and radiate from the center of the dome. Each third pouch has a third enclosing membrane and a third lumen formed by the third enclosing membrane. The third pouches are provided between the second pouches in the first lumen and are arranged in strings that extend from the center of the dome.

12 Claims, 4 Drawing Sheets

100

BREAST IMPLANT

BACKGROUND OF THE INVENTION

1. Technical Field

The present invention relates to a breast implant and more particularly to a modular multi-lumen breast implant system that includes a plurality of relatively small and elastic inner pouches contained within a relatively large and elastic outer pouch so as to imitate the structure and movement of a natural breast.

2. Description of Related Art

Breast cancer is one of the most common cancers among women and, due to the changes in diet and lifestyle of late, has had a higher incidence rate each year. To prevent cancer cells from spreading, some breast cancer patients may choose to undergo mastectomy, followed by breast reconstruction surgery and associated treatments. Consequently, the demand for breast reconstruction and related medical services has risen and drawn much attention.

Moreover, as economy grows and the society becomes more open, and given that it is human nature to desire an attractive look, people nowadays are more demanding on their physical appearance than before. This is why breast augmentation has been a common surgical procedure in pursuit of a visually pleasing body curve. Also, the esthetics of cosmetic breast surgery has improved accordingly.

People who consider breast augmentation want their breasts to not only look natural after the surgery, but also feel natural to the touch. A natural breast is in the shape of a water drop whether the body is in a lying or standing position, and wobbles in a natural and elastic manner when the body moves. The tactile feel of a breast prosthesis depends on the material and implantation position of the prosthesis. Generally, a breast implant is placed under the mammary gland or the pectoralis major.

An unsuccessful breast augmentation may result in stiff breasts, excessive heights of the breast prostheses, uneven appearance in terms of breast size or height, unnatural breast shapes, leakage of the filler material in the breast prostheses, hematoma, bacterial infection, downward slippage of the breast implants, nerve injury, or the possibility that the peripheral fold of the breast implants can be vaguely felt by touching the lower inner edge, lower edge, or outer edge of each breast. It is therefore an important issue in modern esthetic medicine to improve mammaplasty techniques.

BRIEF SUMMARY OF THE INVENTION

To enhance the look and tactile feel of a breast that has undergone augmentation mammoplasty, the present invention provides a breast implant that allows the breast in which the implant is placed to look and feel like a natural breast so that people who have their breasts augmented with such implants will seem to have natural breasts. Unlike the conventional breast implants, the breast implant disclosed herein is visually compatible with the body of one who undergoes breast augmentation surgery, making it possible for an implanted breast to look natural, to have a desirable tactile feel, not to move like a stiff ball as does a breast with a conventional implant, and therefore not to be readily identifiable as a "fake breast".

As above, the present invention provides a breast implant, comprising a first pouch, a plurality of second pouches, and a plurality of third pouches. The first pouch has a first enclosing membrane and a first lumen formed by the first enclosing membrane. The interior of the first lumen includes a dome and a bottom portion corresponding to the dome. Each second pouch has a second enclosing membrane and a second lumen formed by the second enclosing membrane. The second pouches are provided in the first lumen and radiate from the center of the dome. Each third pouch has a third enclosing membrane and a third lumen formed by the third enclosing membrane. The third pouches are provided between the second pouches in the first lumen and are arranged in strings that extend from the center of the dome. The first lumen, the second lumens, and the third lumens are filled with a filler.

In a preferred embodiment, the breast implant includes a plurality of fourth pouches, each having a fourth enclosing membrane and a fourth lumen formed by the fourth enclosing membrane. The fourth pouches are distributed randomly in the first lumen.

In a preferred embodiment, each second pouch is shaped like a water drop; wherein the pointed end is provided at the center of the dome, and the blunt end at the bottom portion of the first lumen.

In a preferred embodiment, the third pouches are connected in series by a plurality of string structures.

In a preferred embodiment, the first enclosing membrane, the second enclosing membranes, the third enclosing membranes, and the fourth enclosing membranes are formed of a biocompatible material.

In a preferred embodiment, the filler is one or more selected from the group consisting of saline water, silicone, and a biocompatible material.

In a preferred embodiment, the saline water is normal saline solutions.

In a preferred embodiment, the silicone is silicone gels.

In a preferred embodiment, the first pouch is disc-shaped or teardrop-shaped.

In a preferred embodiment, the outer side of the first enclosing membrane has a sandy surface.

In a preferred embodiment, the outer side of the first enclosing membrane has a smooth surface.

A conventional breast implant is but a large pouch containing a homogeneous filler. Once implanted, this massive structure is incongruous with the human body and renders the implanted breast artificial-looking, stiff to the touch, and unable to wobble like a natural breast. By contrast, the breast implant of the present invention imitates the internal structure of a human breast so that a breast implanted with the implant will look natural, feel supple rather than lumpy or stiff, have the same softness as a natural breast when pressed, and can wobble in a natural manner. Thus, the drawbacks of the conventional breast implants are overcome.

DETAILED DESCRIPTION OF THE INVENTION

The details and technical solution of the present invention are hereunder described with reference to accompanying drawings. For illustrative sake, the accompanying drawings are not drawn to scale. The accompanying drawings and the scale thereof are not restrictive of the present invention.

The following description should not be seen as an excessive restriction on the present invention. A person having ordinary skill in the art can change and modify the implement discussed in this article without inconsistence of the scope or spirits of the present invention, and the implement with changes and modification of the present invention still fall within the claims of the present invention.

Figure 1:
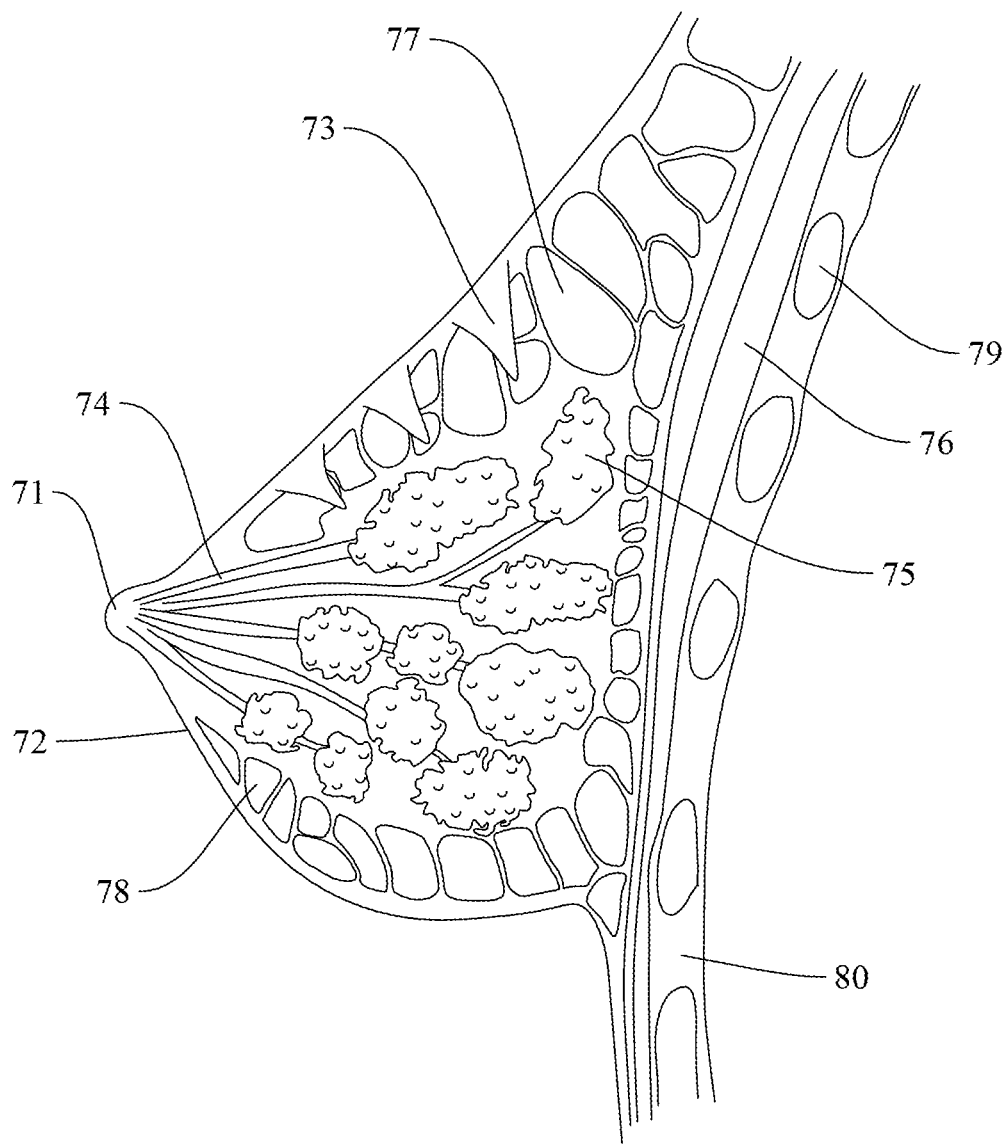
FIG. 1 is a sectional view of a natural human breast.

Please refer to FIG. 1 for a sectional view of a natural human breast. The breast protrudes from the chest, lies adjacent to and in front of the pectoralis major 76 and the ribs 79, and has a nipple 71 and a breast-envelope skin 72 on the outside. The internal tissues of the breast include the Cooper's ligaments 73, a mammary gland, large fatty tissues 77, and small fatty tissues 78. The Cooper's ligaments 73 provide a supporting structure for the breast. The mammary gland includes milk ducts 74, which are distributed in the breast in a radiating manner and are connected with lobules 75. The fatty tissues (i.e. large fatty tissues 77 and small fatty tissues 78), on the other hand, are distributed randomly. The Cooper's ligaments 73 are frame-like structure for supporting natural human breast. The breast is plump, soft, and elastic because of the milk ducts 74, lobules 75, large fatty tissues 77, and small fatty tissues 78 therein. The remaining spaces in the breast are occupied by nerves, blood vessels, and lymphatic vessels (not shown). The breast implant of the present invention imitates a natural breast in structure.

As used herein, the term "outer side of the first enclosing membrane 11" refers to the side of the membrane that is in contact with the human body after the breast implant is implanted into a human breast. Conversely, the term "inner side of the first enclosing membrane 11" refers to the side of the membrane that forms and corresponds to the first lumen 12.

Figure 2:
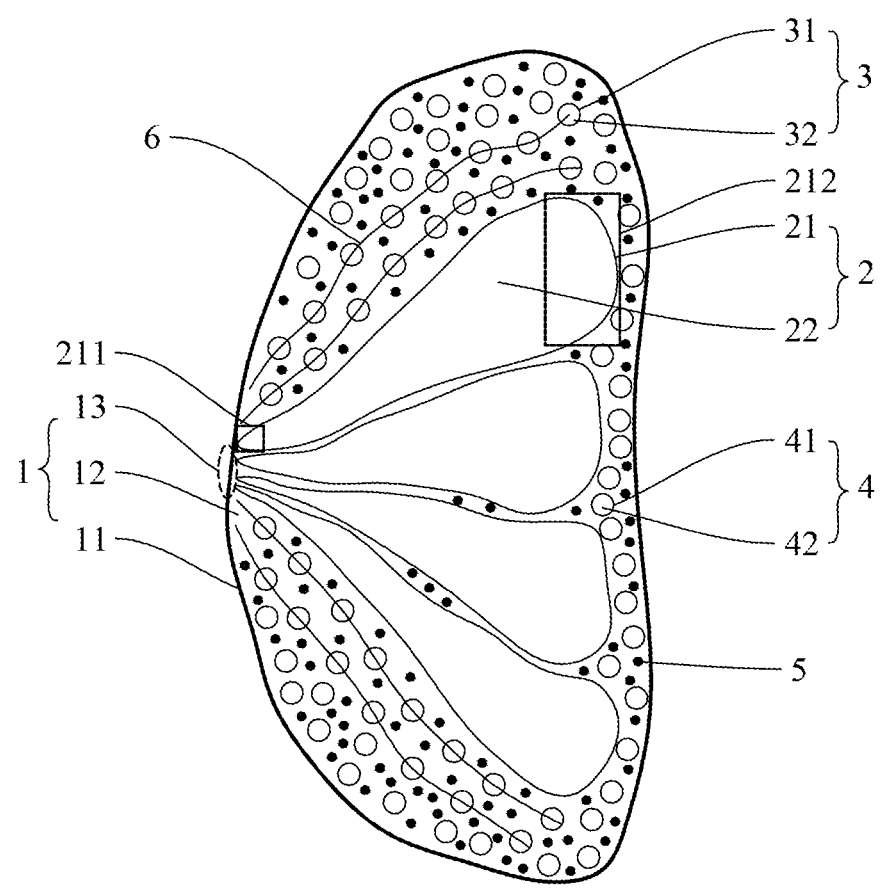
FIG. 2 is a sectional view of a breast implant according to the present invention.
Figure 3:
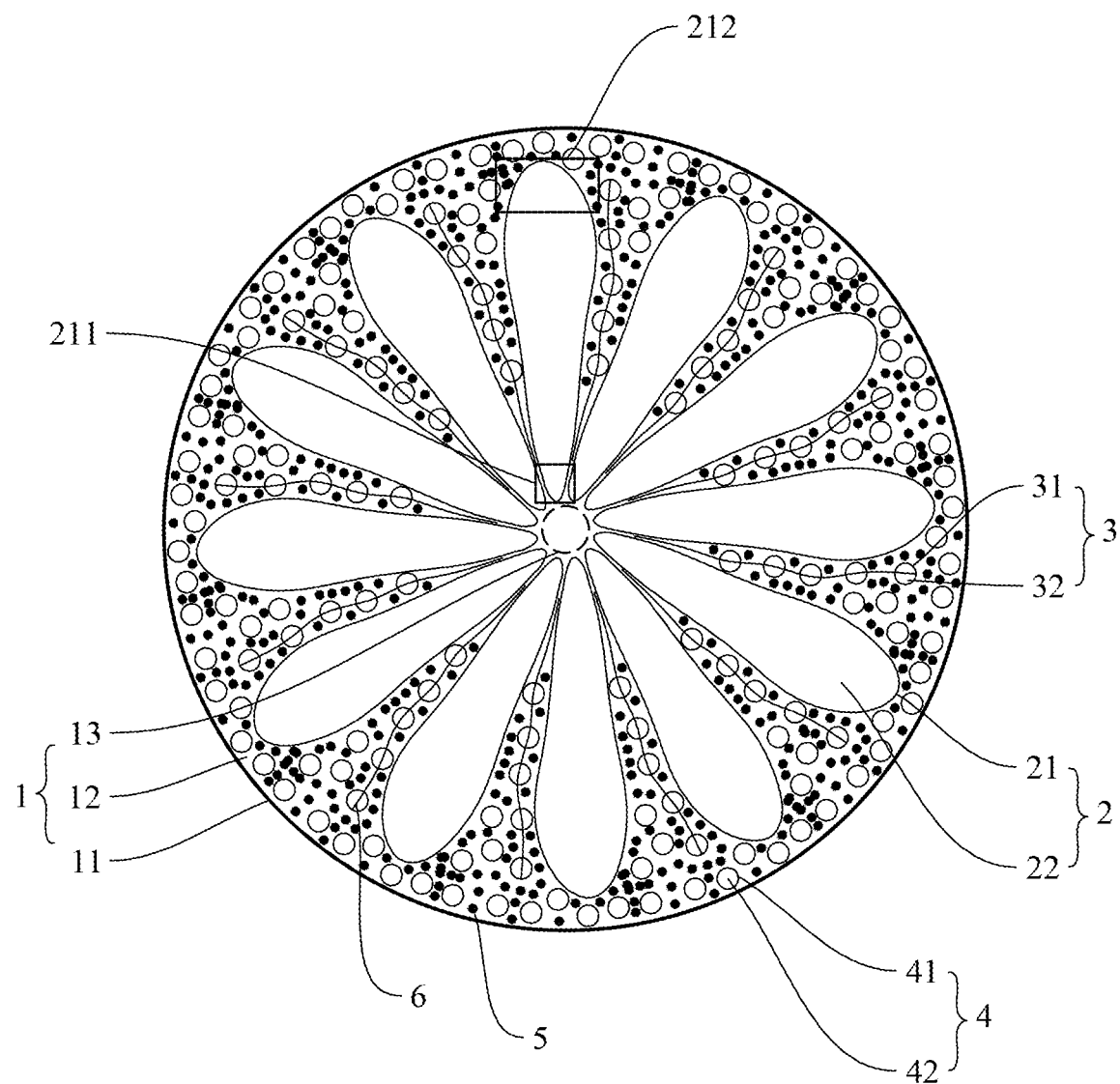
FIG. 3 is a top view of a breast implant according to the present invention.

Please refer to FIG. 2 and FIG. 3 respectively for a sectional view and a top view of a breast implant 100 according to the present invention. The breast implant 100 includes a first pouch 1, a plurality of second pouches 2, and a plurality of third pouches 3. The first pouch 1 has a first enclosing membrane 11 and a first lumen 12 formed by the first enclosing membrane 11. The interior of the first lumen 12 includes a dome 13 and a bottom portion corresponding to the dome 13. Each second pouch 2 has a second enclosing membrane 21 and a second lumen 22 formed by the second enclosing membrane 21. The second pouches 2 are provided in the first lumen 12 and radiate from the center of the dome 13. Each third pouch 3 has a third enclosing membrane 31 and a third lumen 32 formed by the third enclosing membrane 31. The third pouches 3 are provided between the second pouches 2 in the first lumen 12 and are arranged in strings that extend from the center of the dome 13. The first lumen 12, the second lumens 22, and the third lumens 32 are filled with a filler 5.

More specifically, the third pouches 3 are connected in series by a plurality of string structures 6.

The breast implant 100 further includes a plurality of fourth pouches 4, each having a fourth enclosing membrane 41 and a fourth lumen 42 formed by the fourth enclosing membrane 41. The fourth pouches 4 are distributed randomly in the first lumen 12.

The first pouch 1 may be disc-shaped or teardrop-shaped to resemble a natural breast in appearance. Once the breast implant 100 is implanted in a breast, the first pouch 1 enables the breast implant 100 to produce a natural-looking breast shape, rather than the unnatural ball shape attributable to a conventional breast implant. The outer side of the first enclosing membrane 11 may have a sandy surface or a smooth surface. The sandy surface feels grainy (like sandpaper) so as to bond in multiple directions to the internal tissues of the breast in which the breast implant 100 is implanted, thereby preventing capsular contracture, shortening the time required for postoperative massage, or even eliminating the need for such massage. The smooth surface is less likely to cause wrinkles in the breast-envelope skin after the implantation; feels softer, and hence more similar to a natural breast, than the sandy surface; and allows the implanted breast to wobble naturally. The sandy surface and the smooth surface have their respective pros and cons and can be chosen as needed.

The second pouches 2 are shaped like water drops but are not identical in shape to water drops in that each second pouch 2 is strip-like and has a pointed end 211 and a blunt end 212 wider than the pointed end 211. The pointed ends 211 are provided at the center of the dome 13, and the blunt ends 212, at the bottom portion of the first lumen 12 such that the second pouches 2 resemble the mammary gland in a natural breast, or more particularly the milk ducts 74 and the lobules 75, which are arranged in layers in a radiating manner. The second pouches 2 may have the same size (as shown in the drawings) or have different sizes (not shown). Once the breast implant 100 is implanted in a breast, the second pouches 2 enable the breast implant 100 to produce the same tactile feel as a natural breast, i.e., being able to show a smooth and slightly concave indentation when pressed. By contrast, a breast implanted with a conventional breast implant may feel lumpy and taut, or unnatural in short.

The third pouches 3 are intended to simulate the Cooper's ligaments 73 in a natural breast and are therefore preferably connected in series by the string structures 6. The third pouches 3 may have the same size (as shown in the drawings) or have different sizes (not shown). Once the breast implant 100 is implanted in a breast, the third pouches 3 enable the breast implant 100 to produce the three-dimensional shape and firmness of a natural breast and be elastic when pressed. A conventional breast implant, on the other hand, tends to slacken the skin of the breast where it is implanted, is visually incompatible with the breast, and seldom feels elastic when touched.

The fourth pouches 4 are intended to imitate the large fatty tissues 77 and the small fatty tissues 78 in a natural breast and may have the same size (as shown in the drawings) or have different sizes (not shown). Once the breast implant 100 is implanted in a breast, the fourth pouches 4 provide the breast with plumpness and a soft and elastic feel when touched.

The first enclosing membrane 11, the second enclosing membranes 21, the third enclosing membranes 31, and the fourth enclosing membranes 41 may be made, for example, of biocompatible material, silicone film, silicone gel film or polyacrylamide gel film, preferably biocompatible material.

The string structures 6 may be made of any common biocompatible materials, such as but not limited to silicon-based polymers, collagen peptides, gelatin, collagen, sodium alginate, cellulose, polysaccharides, chitin, polylactide, or gels.

The filler 5 may be any common breast implant filler materials, including saline water, silicones, and biocompatible materials, such as but not limited to normal saline solutions, silicone gels, or medical-grade chitosan. If necessary, the filler 5 may be added with an additive such as but not limited to an antibacterial agent, an anti-inflammatory agent (e.g., a glucocorticoid hormone), or a thickening agent (e.g., carboxymethyl cellulose).

Figure 4:
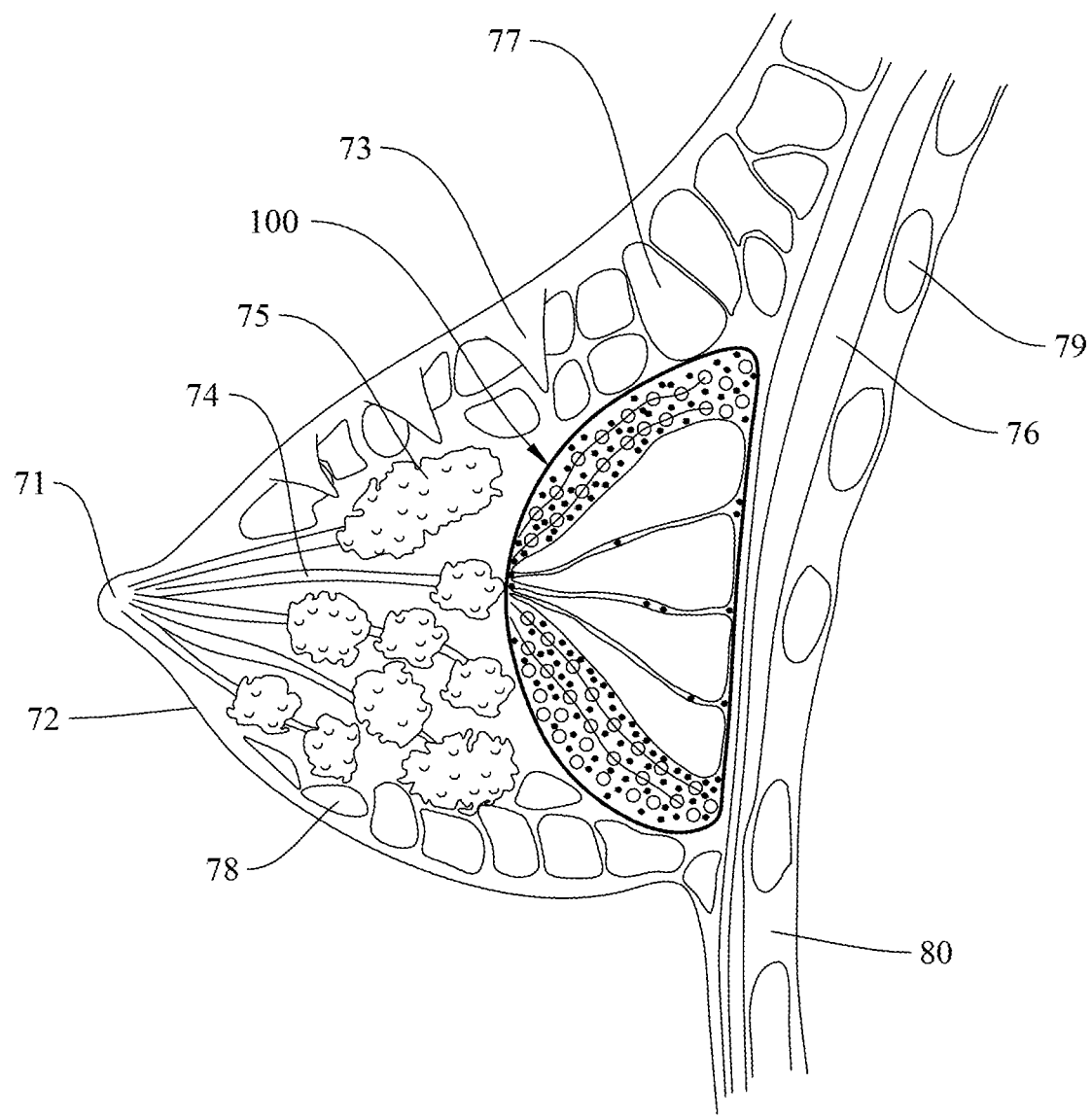
FIG. 4 is a sectional view showing the breast implant of the present invention implanted in a breast.

Please refer to FIG. 4 for a sectional view showing the breast implant 100 implanted in a breast. The breast implant 100 exists as an internal structure of the breast where it is implanted, serving to support, enlarge, and beautify the breast.

The breast implant 100 of the present invention can be implanted into a breast through various incisions in the skin, such as transaxillary, periareola, inframmary fold, and umbilical.

The breast implant 100 of the present invention can be placed at various positions in the breast where it is implanted, such as subglandular, submuscular, or biplane.

The breast implant of the present invention imitates the internal structure of a human breast so that a breast implanted with the implant will look natural, feel supple rather than lumpy or stiff, have the same softness as a natural breast when pressed, and can wobble in a natural manner. Thus, the drawbacks of the conventional breast implants are overcome.

The above is the detailed description of the present invention. However, the above is merely the preferred embodiment of the present invention and cannot be the limitation to the implement scope of the present invention, which means the variation and modification according to the present invention may still fall into the scope of the invention.

What is claimed is:

1. A breast implant, comprising:
   a first pouch having a first enclosing membrane and a first lumen formed by the first enclosing membrane, wherein the first lumen has therein a dome and a bottom portion corresponding to the dome;
   a plurality of second pouches, each having a second enclosing membrane and a second lumen formed by the second enclosing membrane, wherein the second pouches are provided in the first lumen and radiate from a center of the dome; and
   a plurality of third pouches, each having a third enclosing membrane and a third lumen formed by the third enclosing membrane, wherein the third pouches are provided between the second pouches in the first lumen and are arranged in strings extending from the center of the dome;
   wherein the first lumen, the second lumens, and the third lumens are filled with a filler.

2. The breast implant of claim 1, wherein the breast implant further includes a plurality of fourth pouches, each having a fourth enclosing membrane and a fourth lumen formed by the fourth enclosing membrane; and, the fourth pouches are distributed randomly in the first lumen.

3. The breast implant of claim 1, wherein each of the second pouch is shaped like a water drop; wherein the pointed end is provided at the center of the dome, and the blunt end at the bottom portion of the first lumen.

4. The breast implant of claim 1, wherein the third pouches are connected in series by a plurality of string structures.

5. The breast implant of claim 1, wherein the first enclosing membrane, the second enclosing membranes, or the third enclosing membranes are formed of a biocompatible material.

6. The breast implant of claim 2, wherein the fourth enclosing membranes are formed of a biocompatible material.

7. The breast implant of claim 1, wherein the filler is one or more selected from the group consisting of saline water, silicone, and a biocompatible material.

8. The breast implant of claim 7, wherein the saline water is normal saline solutions.

9. The breast implant of claim 7, wherein the silicone is silicone gels.

10. The breast implant of claim 1, wherein the first pouch is disc-shaped or teardrop-shaped.

11. The breast implant of claim 1, wherein the outer side of the first enclosing membrane has a sandy surface.

12. The breast implant of claim 1, wherein the outer side of the first enclosing membrane has a smooth surface.

* * * * *